United States Patent
Oikawa et al.

(10) Patent No.: US 10,639,011 B2
(45) Date of Patent: *May 5, 2020

(54) SUBJECT INFORMATION ACQUISITION APPARATUS

(71) Applicant: CANON KABUSHIKI KAISHA, Tokyo (JP)

(72) Inventors: Katsuya Oikawa, Tokyo (JP); Kenichi Nagae, Yokohama (JP); Makoto Yamakawa, Kyoto (JP); Tsuyoshi Shiina, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/490,776

(22) Filed: Apr. 18, 2017

(65) Prior Publication Data
US 2017/0215847 A1 Aug. 3, 2017

Related U.S. Application Data

(63) Continuation of application No. 14/110,125, filed as application No. PCT/JP2012/059952 on Apr. 5, 2012, now Pat. No. 9,655,589.

(30) Foreign Application Priority Data

Apr. 8, 2011 (JP) ................. 2011-086512

(51) Int. Cl.
A61B 8/08 (2006.01)
A61B 8/00 (2006.01)
G01S 7/52 (2006.01)

(52) U.S. Cl.
CPC ............. A61B 8/485 (2013.01); A61B 8/085 (2013.01); A61B 8/0858 (2013.01); A61B 8/4483 (2013.01); A61B 8/5223 (2013.01); A61B 8/585 (2013.01); G01S 7/52042 (2013.01)

(58) Field of Classification Search
CPC ....... A61B 8/485; A61B 8/4483; A61B 8/585; A61B 8/0858; A61B 8/5223; A61B 8/085; G01S 7/52042
USPC .................................. 600/437–469
See application file for complete search history.

(56) References Cited

U.S. PATENT DOCUMENTS

| | | | |
|---|---|---|---|
| 9,289,186 B2* | 3/2016 | Tashiro | A61B 8/44 |
| 2008/0267499 A1* | 10/2008 | Deischinger | G06K 9/3233 |
| | | | 382/173 |
| 2010/0160778 A1* | 6/2010 | Eskandari | A61B 8/00 |
| | | | 600/438 |
| 2011/0040185 A1* | 2/2011 | Matsumura | A61B 8/00 |
| | | | 600/443 |

(Continued)

Primary Examiner — Sanjay Cattungal
(74) Attorney, Agent, or Firm — Canon U.S.A., Inc., IP Division

(57) ABSTRACT

Viscoelastic characteristics in a subject are imaged by a simple method. A viscoelasticity measurement reference layer whose elastic modulus and viscosity coefficient are known is included between an ultrasonic wave transmitting/receiving probe and the subject and distributions of elastic modulus and viscosity coefficient inside the subject are calculated from a change over time of strain generated in the viscoelasticity measurement reference layer and the subject according to a pressure applied to the subject which changes over time and known elastic modulus and viscosity coefficient of the viscoelasticity measurement reference layer.

24 Claims, 4 Drawing Sheets

(56) References Cited

U.S. PATENT DOCUMENTS

2014/0221833 A1\* 8/2014 Oikawa ................ A61B 8/485
                                                          600/438

\* cited by examiner

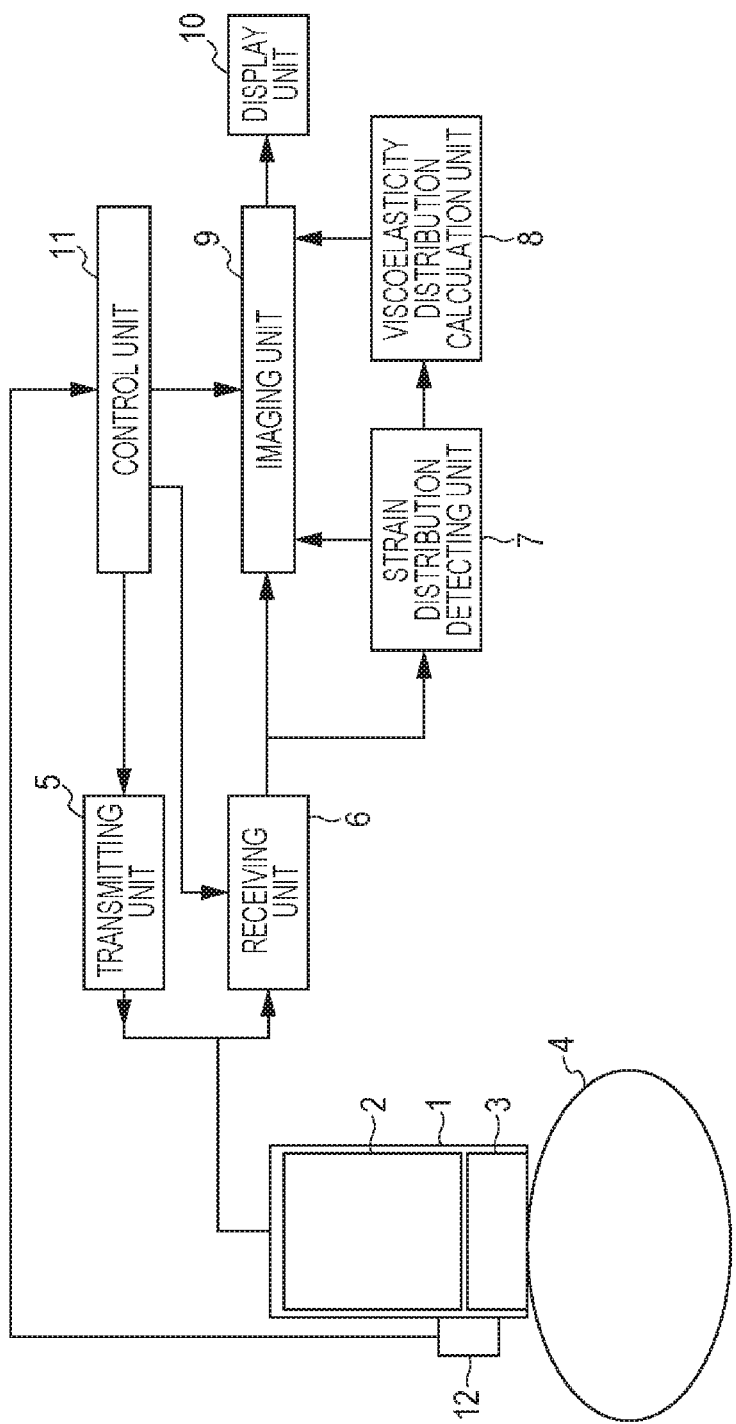

SUBJECT INFORMATION ACQUISITION APPARATUS

CROSS-REFERENCE TO RELATED APPLICATIONS

This application is a Continuation of co-pending U.S. patent application Ser. No. 14/110,125 filed Mar. 6, 2014, which is a U.S. national stage application of International Patent Application No. PCT/JP2012/059952, filed Apr. 5, 2012, which claims foreign priority benefit of Japanese Patent Application No. 2011-086512, filed Apr. 8, 2011. All of the above-named patent applications are hereby incorporated by reference herein in their entirety.

TECHNICAL FIELD

The present invention relates to a subject information acquisition apparatus, in particular to a subject information acquisition apparatus for imaging viscoelastic characteristics of a subject.

BACKGROUND ART

An ultrasonic diagnostic apparatus is known as a subject information acquisition apparatus. The ultrasonic diagnostic apparatus noninvasively images information inside the subject, so that the ultrasonic diagnostic apparatus is widely used in the medical field.

In the ultrasonic diagnostic apparatus, an ultrasonic cross-sectional image in which a structure in a biological body is imaged from reflection echo generated by differences of reflectivity of tissues and a Doppler ultrasound image in which a blood flow velocity or the like is imaged by using an ultrasonic Doppler effect generated by a blood flow are conventionally used.

Further, recently, hardness of tissue is measured by an ultrasonic wave and the hardness is used to diagnose the tissue. This is because the hardness of tissue deeply related to a pathological state. For example, it is known that a sclerosing cancer such as breast cancer and thyroid cancer is harder than a normal tissue and a benign tumor.

In recent years, it is reported that viscosity is different between cancer and a benign tumor, so that not only tissue hardness measurement, but also viscoelastic characteristics evaluation including viscosity characteristics evaluation is required for tissue diagnosis. Therefore, it is required to measure distribution of viscoelastic characteristics in a biological body by using ultrasonic wave, form the distribution into an image, combine the image with a conventional image of tissue structure, and use the combined images to diagnose cancer or the like in a tissue.

As an ultrasonic diagnostic apparatus for calculating the viscosity of the subject, PTL 1 discloses an apparatus that uses an ultrasonic probe in which a pressure sensor is provided on a surface of a transducer transmitting and receiving an ultrasonic wave, measures strain distribution by ultrasonic wave, measures pressure distribution applied to the subject by the pressure sensor, and calculates values of elasticity and viscosity from the strain distribution and the pressure distribution.

As a method for measuring pressure, PTL 2 discloses an ultrasonic diagnostic apparatus in which a pressure measuring deformation portion whose elastic modulus is known is sandwiched between an ultrasonic probe and a biological tissue to measure pressure. The ultrasonic diagnostic apparatus measures deformation of the pressure measuring deformation portion by ultrasonic wave, calculates pressure (stress) applied to the pressure measuring deformation portion from a relationship between elastic modulus and strain, calculates elastic modulus distribution in the subject from the stress and strain distribution in the subject, and displays the elastic modulus distribution.

However, in the configuration described in PTL 1, the structure of the ultrasonic probe is complicated. Further, generally when strain distribution in a tissue is measured by using ultrasonic wave, applied pressure is very small, so that it is difficult for a normal pressure sensor to measure the pressure. Furthermore, if the pressure sensor is inserted immediately below the ultrasonic probe, efficiency and sensitivity of transmitting and receiving ultrasonic wave degrade, so that there is a problem that measurement of deep portion cannot be performed.

In PTL 2, although the configuration of the apparatus is simple, only the elasticity distribution in the subject is displayed and a method for measuring the viscosity distribution in the subject is not disclosed. Therefore, an apparatus which has a simple configuration and which can calculate viscosity of the subject is required.

CITATION LIST

Patent Literature

PTL 1 Japanese Patent Laid-Open No. 2007-222605
PTL 2 Japanese Patent Laid-Open No. 2005-66041

SUMMARY OF INVENTION

The present invention that can solve the above problem is a subject information acquisition apparatus for transmitting an elastic wave to a subject, receiving the elastic wave reflected from inside the subject, and acquiring information inside the subject. The subject information acquisition apparatus includes a conversion device that receives the elastic wave and converts the elastic wave into an electrical signal, a reference layer which is provided between the conversion device and the subject and whose viscosity coefficient ($\eta c$) and elastic modulus ($Ec$) are known, a measuring unit that measures strain ($\varepsilon$) of the subject and strain ($\varepsilon c$) of the reference layer which are generated when a pressure is applied to the subject and the reference layer by using the electrical signal, and a calculation unit that calculates a viscosity coefficient ($\eta$) of the subject by using a viscosity coefficient ($\eta c$) and an elastic modulus ($Ec$) of the reference layer, the strain ($\varepsilon$) of the subject, and the strain ($\varepsilon c$) of the reference layer.

Advantageous Effects of Invention

The present invention can provide a subject information acquisition apparatus, such as an ultrasonic diagnostic apparatus, which can measure highly-sensitive and high-resolution strain distribution, calculate distributions of Young's modulus and viscous coefficient from measurement of stress distribution based on the strain distribution, and image distribution of viscoelastic characteristics in a biological body even though having a simple apparatus configuration.

BRIEF DESCRIPTION OF DRAWINGS

FIG. 1 is a block diagram showing an ultrasonic diagnostic apparatus, which is a subject information acquisition apparatus of the present invention.

DESCRIPTION OF EMBODIMENTS

Figure 2A:
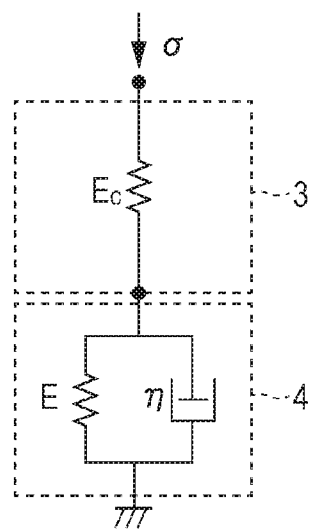
FIGS. 2A and 2B are diagrams showing a principle of viscoelasticity measurement of the present invention.

Hereinafter, an embodiment of the present embodiment will be described in detail with reference to the drawings.

FIG. 1 is a block diagram showing an ultrasonic diagnostic apparatus which is a subject information acquisition apparatus of the present embodiment. The ultrasonic diagnostic apparatus displays an image based on a viscoelasticity distribution of biological tissue, in particular based on a viscosity coefficient distribution in addition to an elastic modulus distribution, along with a cross-sectional image of a diagnostic region of a subject by using an ultrasonic wave. In particular, in an example shown in FIG. 1, strains of a viscoelasticity measurement reference layer and the subject are measured by periodically pressing the subject through a probe by an operator using a hand-held type probe described later. A viscoelasticity distribution of the subject is calculated by using the strain of the viscoelasticity measurement reference layer, the strain of the subject, and known elastic modulus and viscosity coefficient of the viscoelasticity measurement reference layer, and the calculation result is displayed.

In FIG. 1, reference numeral 1 denotes a probe including a conversion element array 2 that is a conversion device which doubles as a unit that transmits an ultrasonic wave as an elastic wave to a subject 4 and a unit that receives an ultrasonic wave as an elastic wave reflected by the subject 4 and converts the ultrasonic wave into an electrical signal and a viscoelasticity measurement reference layer 3 which is provided between the conversion element array 2 and the subject 4 and whose viscosity coefficient (ηc) and elastic modulus (Ec) are known. Reference numeral 4 denotes the subject, reference numeral 5 denotes a transmitting unit that transmits a control signal to the probe 1, and reference numeral 6 denotes a receiving unit that receives an electrical signal from the conversion device included in the probe 1. Reference numeral 7 is a strain distribution detecting unit that is a measuring unit which measures a strain of the subject 4 and a strain of the viscoelasticity measurement reference layer 3 generated when a pressure is applied to the subject 4 and the viscoelasticity measurement reference layer 3 by using an electrical signal from the conversion device included in the probe 1. Reference numeral 8 is a viscoelasticity distribution calculation unit that is a calculation unit which calculates the viscosity coefficient of the subject 4 by using a measured strain of the viscoelasticity measurement reference layer 3, a measured strain of the subject 4, and the known viscosity coefficient and elastic modulus of the viscoelasticity measurement reference layer 3. Further, the configuration of FIG. 1 includes an imaging unit 9, a display unit 10, and a control unit 11 as an embodiment. The probe 1 also includes a control switch 12 that controls an operation of calculating the viscoelasticity distribution. Hereinafter, the principle of calculating the viscosity coefficient of the subject 4 by the above-described ultrasonic diagnostic apparatus will be described.

In the embodiment of the present invention, the probe 1 periodically applies a pressure to the subject by manual operation or mechanical driving, and at the same time, the probe 1 transmits and receives an ultrasonic wave as an elastic wave to and from the subject through the viscoelasticity measurement reference layer 3 whose elastic modulus and viscosity coefficient are known, so that a strain distribution in the viscoelasticity measurement reference layer 3 and a strain distribution in the subject 4 are measured.

When a tissue has no viscosity, an amplitude value of strain periodically generated in the tissue of the subject 4 when a pressure is periodically applied to the subject 4 is represented by the following equation.

[Math. 1]

$$\varepsilon = \frac{\sigma_0}{E} \qquad \text{(Equation 1)}$$

Here, E is an elastic constant (Young's modulus) of the tissue and $\sigma_0$ is an amplitude of a stress (pressure) which is periodically applied. Therefore, when the tissue has no viscosity, the elasticity of the tissue can be obtained from the amplitude value of the strain. Conversely, when the viscoelasticity measurement reference layer 3 has no viscosity, the stress can be obtained from the amount of strain.

On the other hand, when a tissue has a viscosity, for example, if a periodic pressure having a triangular waveform with respect to time is applied, the amplitude value of the periodic strain generated in the tissue is represented by the following equation.

[Math. 2]

$$\varepsilon = \frac{2\tau\sigma_0}{ET}\left[2\ln\left(e^{\frac{T}{2\tau}}+1\right)-\frac{T}{2\tau}-2\ln 2\right] \qquad \text{(Equation 2)}$$

Here, $\tau$ is a ratio of the viscosity coefficient and the Young's modulus of the tissue and T is a period of the pressure which is periodically applied. As described above, the value obtained from the measurement of the strain is a ratio of the Young's modulus and the viscosity coefficient, so that the Young's modulus and the viscosity coefficient cannot be obtained separately. Therefore, it is necessary to calculate the viscoelasticity of the subject 4 by using measured values of strain and stress while measuring variation of the strain and stress changing over time in time series by periodically pressing the subject 4. At this time, periodic amplitude of the strain of the viscoelasticity measurement reference layer 3 is represented by the following equation due to the viscosity in the layer.

[Math. 3]

$$\varepsilon_c = \frac{2\tau_c\sigma_0}{E_c T}\left[2\ln\left(e^{\frac{T}{2\tau_c}}+1\right)-\frac{T}{2\tau_c}-2\ln 2\right] \qquad \text{(Equation 3)}$$

It is understood that both (Equation 2) and (Equation 3) approximately approach (Equation 1) when the period is very large (T→∞), that is, when the measurement is performed by spending sufficient time. (Therefore, if the period of the pressure is set to be sufficiently long, at least the Young's modulus can be measured by using (Equation 1)). However, for normal tissue and the viscoelasticity measurement reference layer 3, the ratios $\tau$ and $\tau_c$ of the Young's modulus and the viscosity coefficient are a time from several seconds to several tens of seconds. If a period sufficiently larger than the time is used, the measurement period becomes a long time such as several minutes, so that it is difficult to use (Equation 1) for actual measurement. (Further, in this case, the viscosity coefficient cannot be measured.)

Figure 2B:
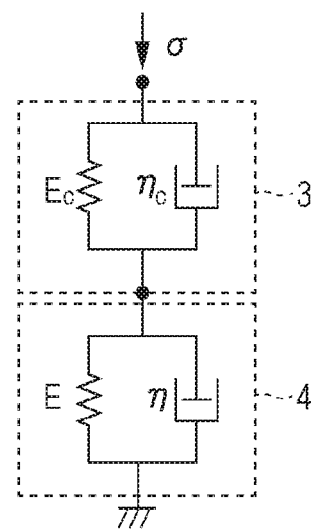

Next, a case in which the viscoelasticity of the subject is temporarily calculated by using a technique described in PTL 2 and a calculation of the viscoelasticity of the subject 4 on the basis of the present embodiment will be described while comparing both calculations. FIGS. 2A and 2B show principles of a case in which the viscoelasticity of the subject is measured on the basis of PTL 2 and a case of the viscoelasticity measurement based on the present embodiment. FIG. 2A is a dynamic model of the viscoelasticity measurement of the subject based on the PTL 2. FIG. 2B is a dynamic model of the viscoelasticity measurement of the subject 4 based on the present invention. In FIG. 2A, the viscosity of the viscoelasticity measurement reference layer is not considered, so that a stress 6 applied to the subject is obtained by multiplying a measured strain by a known Young's modulus Ec of the viscoelasticity measurement reference layer as shown in (Equation 1). If only the elasticity of the subject is measured when temporal change converges after a long time such as several minutes to more than a dozen minutes has elapsed, as described in PTL 2, the stress obtained by using the measured strain of the viscoelasticity measurement reference layer and the Young's modulus of the subject obtained by using the stress are values according to (Equation 1). However, it is difficult in practice to perform such a long time measurement by an ultrasonic diagnostic apparatus using a hand-held probe because the measurement time is too long. Further, as an essential problem, it is necessary to measure changes in strain and stress over time in order to obtain the viscosity of the subject. Specifically, in the strain and the stress after a long time has elapsed, effects of the viscosity of not only the viscoelasticity measurement reference layer, but also the subject disappear, so that it is necessary to measure changes over time in a short time interval. In this case, the subject and the viscoelasticity measurement reference layer individually change over time on the basis of their viscoelasticities respectively, so that it is necessary to perform the measurement according to the dynamic model shown in FIG. 2B. In particular, when using a member having excellent ultrasound propagation characteristics and the same acoustic characteristics as those of the subject to suppress reflection at the boundary as the viscoelasticity measurement reference layer, if the viscosity of the viscoelasticity measurement reference layer is neglected, a large error occurs in the actual measurement. Therefore, when using a viscoelasticity measurement reference layer formed of a practical member, it is difficult to independently obtain the stress from only the Young's modulus of the viscoelasticity measurement reference layer.

On the other hand, as in the present embodiment, when the Young's modulus Ec and the ratio $\tau_c$ of the Young's modulus and the viscosity coefficient of the viscoelasticity measurement reference layer 3 are known, the stress amplitude $\sigma_0$ is obtained from the amplitude $\varepsilon_c$ of periodic strain of the viscoelasticity measurement reference layer 3 by using (Equation 3). Specifically, the strains of the viscoelasticity measurement reference layer 3 are measured over the positions of the viscoelasticity measurement reference layer 3. The strain amplitude $\varepsilon_c$ is obtained by measuring the maximum and minimum values of the strains and the stress amplitude $\sigma_0$ is obtained from (Equation 3).

When more general pressure is applied, the change over time of the stress applied to the tissue is represented by the following equation.

[Math. 4]

$$\sigma(t) = E_c \varepsilon_c(t) + \eta_c \frac{d\varepsilon_c(t)}{dt} \quad \text{(Equation 4)}$$

Here, $\sigma(t)$ and $\varepsilon_c(t)$ are changes over time of the stress and the strain of the viscoelasticity measurement reference layer 3. $\varepsilon_c$ and $\eta_c$ are the known Young's modulus and viscosity coefficient of the viscoelasticity measurement reference layer 3.

Therefore, it is possible to obtain the change of the stress from the strain of the viscoelasticity measurement reference layer 3 measured over at least one cycle of the pressure by using (Equation 4) and obtain the stress amplitude $\sigma_0$ from the amplitude of the change of the stress.

In an example of the present embodiment, the strain distributions in the subject 4 and the viscoelasticity measurement reference layer 3 are measured in time series. Thereby, the changes over time of an amount of strain of a specific tissue in the subject 4 and an amount of strain of a region that presses the tissue in the viscoelasticity measurement reference layer 3 are compared and a time shift (delay time) between both amounts of strain is calculated. At this time, the delay time between both amounts of strain can be represented by the following equation.

[Math. 5]

$$\Delta t = (\tau - \tau_c)\ln 2 - \tau \ln\left(e^{\frac{T}{2\tau}} + 1\right) + \tau_c \ln\left(e^{\frac{T}{2\tau_c}} + 1\right) \quad \text{(Equation 5)}$$

Here, $\tau$ is a ratio of the viscosity coefficient and the Young's modulus of the tissue in the subject 4 and $\tau_c$ is a ratio of the viscosity coefficient and the Young's modulus of the viscoelasticity measurement reference layer 3. When the viscosity coefficient and the Young's modulus of the viscoelasticity measurement reference layer 3 are known, the ratio $\tau$ of the viscosity coefficient and the Young's modulus of the tissue are obtained from (Equation 5) and the Young's modulus E of the subject 4 is calculated from the stress amplitude $\sigma_0$ obtained in the above description and the measured amplitude of strain of the subject 4 by using (Equation 2). Further, the viscosity coefficient of the subject 4 is calculated from the Young's modulus E of the subject 4 and the ratio $\tau$ of the viscosity coefficient and the Young's modulus.

Further, another method for obtaining the ratio T of the viscosity coefficient and the Young's modulus of the tissue in the subject 4 will be described with reference to FIGS. 3A, 3B, and 3C.

Figure 3A:
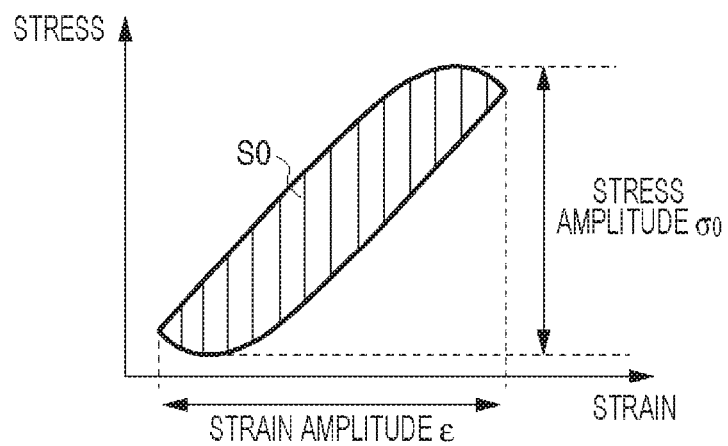
FIGS. 3A to 3C are diagrams for explaining an area of hysteresis loop according to the present invention.

When the strain and the stress are measured while a periodic pressure is applied and the values of the strain and the stress are plotted on a graph, a hysteresis loop as shown in FIG. 3A is depicted. An area S0 of the hysteresis loop is a function of the ratio $\tau$ of the viscosity coefficient and the Young's modulus. The viscosity may be obtained from the area of the hysteresis loop in this way. Further, a hysteresis loop formed by periodic changes of the strains of the viscoelasticity measurement reference layer 3 and the subject 4 may be used to avoid troublesome calculation of the changes over time of the stress. FIG. 3B shows a graph in which the strains of the viscoelasticity measurement reference layer 3 and the subject 4 are plotted while a periodic pressure is applied. Also in this case, a hysteresis loop is formed, and for example, when a periodic pressure having a triangular waveform with respect to time is applied as described above, an area S1 of the hysteresis loop is represented by the following equation.

[Math. 6]

$$S1 = \frac{4\sigma_0}{EE_c T^2}\left\{(\tau_c - \tau)T + 4\frac{\tau_c - \tau}{\tau_c + \tau}\tau\tau_c + 4(\tau^2 - \tau_c^2) + \frac{8}{\tau_c + \tau}\left[\frac{\tau_c^3}{e^{\frac{T}{2\tau_c}} + 1} - \frac{\tau^3}{e^{\frac{T}{2\tau}} + 1}\right]\right\}$$ (Equation 6)

When (Equation 2) and (Equation 3) are applied the above equation, the following equation is established.

[Math. 7]

$$S1 = \frac{\varepsilon\varepsilon_c\left\{(\tau_c - \tau)T + 4\frac{\tau_c - \tau}{\tau_c + \tau}\tau\tau_c + 4(\tau^2 - \tau_c^2) + \frac{8}{\tau_c + \tau}\left[\frac{\tau_c^3}{e^{\frac{T}{2\tau_c}} + 1} - \frac{\tau^3}{e^{\frac{T}{2\tau}} + 1}\right]\right\}}{\left[2\ln\left(e^{\frac{T}{2\tau}} + 1\right) - \frac{T}{2\tau} - 2\ln 2\right]\left[2\ln\left(e^{\frac{T}{2\tau_c}} + 1\right) - \frac{T}{2\tau_c} - 2\ln 2\right]}$$ (Equation 7)

Here, T is a period of the periodic pressure, E and E are respectively the amplitude of strain of the viscoelasticity measurement reference layer 3 and the amplitude of strain of the subject 4 which are obtained by measurement, and $\tau_c$ is the ratio of the known viscosity coefficient and Young's modulus of the viscoelasticity measurement reference layer 3. Therefore, the area S1 of the hysteresis loop of the left-hand side and values of each variable in the right-hand side can be measured by measuring strain except for $\tau$. Thus, the value of $\tau$ can be obtained by reversely solving this equation.

In particular, if the period T is set to a short time of about several seconds and periodical pressure is applied, the following approximate equation can be used.

[Math. 8]

$$S1 = \frac{\varepsilon\varepsilon_c\left\{(\tau_c - \tau)T + 4\frac{\tau_c - \tau}{\tau_c + \tau}\tau\tau_c + 4(\tau^2 - \tau_c^2) + \frac{8}{\tau_c + \tau}\left[\frac{\tau_c^3}{2\tau_c + 2} - \frac{\tau^3}{\frac{T}{2\tau} + 2}\right]\right\}}{\left[2\ln\left(\frac{T}{2\tau} + 2\right) - \frac{T}{2\tau} - 2\ln 2\right]\left[2\ln\left(\frac{T}{2\tau_c} + 2\right) - \frac{T}{2\tau_c} - 2\ln 2\right]}$$ (Equation 8)

Further, a hysteresis parameter described in (Reference Document 1) Nitta, Shiina, Ueno, "Hysteresis Parameter Imaging of Soft Tissue under Quasi-Static Deformation", 2003 IEEE International Ultrasonics Symposium Proceedings, pp. 1606-1609, 2003 may be used.

Figure 3B:
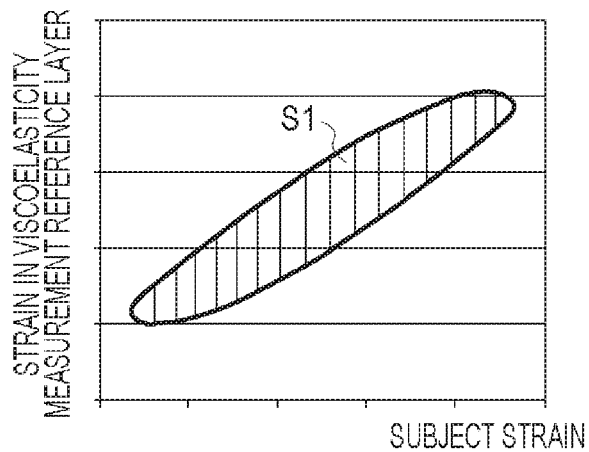
Figure 3C:
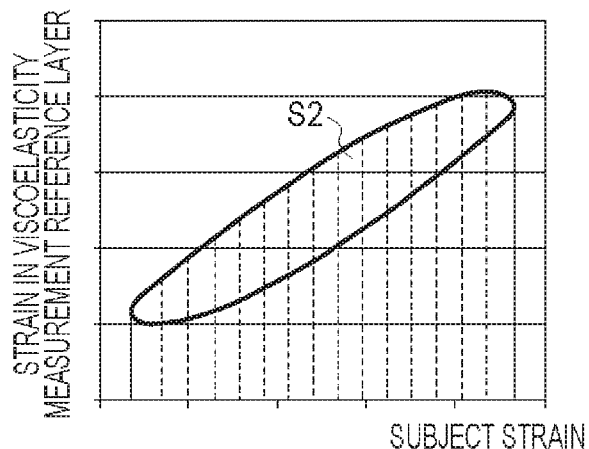

FIG. 3C is a diagram showing how to obtain a reference area S2 for calculating a hysteresis parameter.

FIG. 3C is a graph in which the strains of the viscoelasticity measurement reference layer 3 and the subject 4 are plotted while a periodic pressure is applied in the same manner as in FIG. 3B. The area S2 surrounded by the maximum value and the minimum value of the strain of the subject 4 is calculated. A hysteresis parameter HP can be obtained by calculating a ratio of the area of the hysteresis loop to the reference area S2 as shown by the following equation.

[Math. 9]

$$HP = \frac{S1}{S2}$$ (Equation 9)

The value of $\tau$ can be obtained by using the hysteresis parameter HP in the same manner as described above. When the hysteresis parameter is used, calculation is standardized by the reference area, so that there is an advantage that there is not so much effect of error in the measurement. Further, when the value of $\tau$ is obtained by reversely solving the equation, there is an advantage that multiple value function is difficult to be generated in general and process is simple.

In the description here, equations related to a case in which a periodical pressure having a triangular waveform with respect to time is applied are shown for simplicity of the description. However, the pressing method may be a method of periodically repeating pressing and releasing and the equations used in the above calculation according to a pattern of change over time may be used for an analysis formula based on the model shown in FIG. 2B and a table of fitting obtained by simulation. Further, a table of fitting obtained by actually measuring the viscoelasticity measurement reference layer may be used.

As a measuring method of another embodiment of the present invention, it is possible to apply pressure in a step-like manner instead of periodically applying pressure and measure the strain distributions in the subject 4 and the viscoelasticity measurement reference layer 3 in time series. Pressure is applied instantaneously and thereafter the strain distributions in the subject 4 and the viscoelasticity measurement reference layer 3 are measured in time series. Even when pressure is applied instantaneously, the effects of the viscosity of the viscoelasticity measurement reference layer 3 are removed after sufficient time has elapsed. However, it is not practical because the measurement time is too long. Therefore, changes over time of the strain value are measured in a short time interval in the same manner as in the case in which pressure is applied periodically.

At this time, in the model shown in FIG. 2B, change over time of strain ε'(t) of the viscoelasticity measurement reference layer 3 and change over time of strain $\varepsilon_c'(t)$ in the subject 4 are represented by the following equations.

[Math. 10]

$$\varepsilon_c'(t) = \frac{\sigma_0}{E_c}\left(1 - e^{-\frac{t}{\tau_c}}\right)$$ (Equation 10)

-continued

[Math. 11]

$$\varepsilon'(t) = \frac{\sigma_0}{E}\left(1 - e^{-\frac{t}{\tau}}\right)$$ (Equation 11)

The stress amplitude $\sigma_0$ is obtained from the measured strain of the viscoelasticity measurement reference layer 3 and the known Young's modulus and viscosity coefficient by using (Equation 10). Further, the ratio $\tau$ of the viscosity coefficient and the Young's modulus is obtained from the measured change of the strain of the subject 4. Specifically, the logarithm of the time derivative of the strain of the subject 4 is calculated by the equation described below.

[Math. 12]

$$\ln\left[\frac{d}{dt}\varepsilon'(t)\right] = -\frac{t}{\tau} + \ln\left(\frac{\sigma_0}{\tau E}\right)$$ (Equation 12)

Therefore, the reciprocal number of the ratio $\tau$ of the viscosity coefficient and the Young's modulus, which is an inclination of the logarithms of the time derivative of the strain of the subject 4 at a plurality of different time points, from the logarithms of the time derivative. When the reciprocal number of the ratio $\tau$ is applied to (Equation 11), the Young's modulus of the subject 4 is obtained, and the viscosity coefficient of the subject 4 is calculated from the Young's modulus and the ratio $\tau$.

Figure 4:
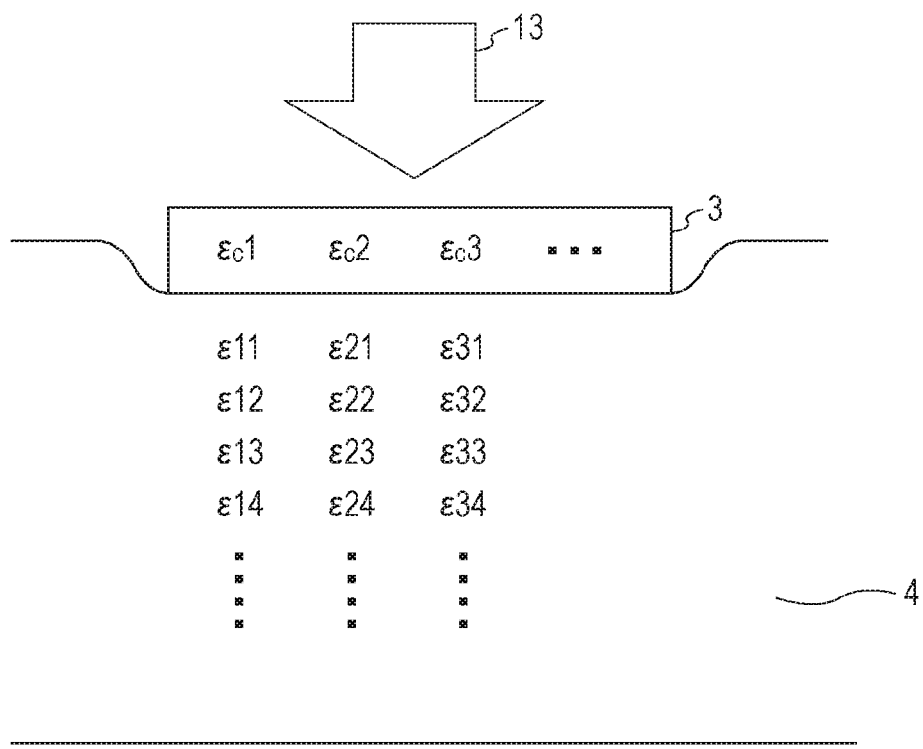
FIG. 4 is a diagram for explaining viscoelasticity distribution measurement according to the present invention.

A method for applying the measurement (calculation) of the Young's modulus and the viscosity coefficient to viscoelasticity distribution measurement (calculation) of the subject 4 will be described with reference to FIG. 4. In FIG. 4, reference numeral 3 denotes the viscoelasticity measurement reference layer, reference numeral 4 denotes the subject, and reference numeral 13 denotes pressure applied for the measurement. The pressure 13 is applied substantially perpendicular to the boundary between the viscoelasticity measurement reference layer 3 and the subject 4 and strain occurs in tissues in the viscoelasticity measurement reference layer 3 and the subject 4 in a vertical direction (a direction of the pressure 13) in FIG. 4. In the viscoelasticity measurement reference layer 3, a strain distribution of $\varepsilon_c 1$, $\varepsilon_c 2$, $\varepsilon_c 3$, and so forth occurs along the boundary, and in the subject 4, a strain distribution of $\varepsilon 11$, $\varepsilon 12$, $\varepsilon 13$, and so forth occurs. Changes over time of these strain distributions are measured by an ultrasonic wave as an elastic wave. The pressure 13 is applied in the vertical direction in FIG. 4, so that the strain $\varepsilon_c 1$ of the viscoelasticity measurement reference layer 3 and the strains $\varepsilon 11$, $\varepsilon 12$, $\varepsilon 13$, and so forth of the subject 4, which are aligned in the vertical direction, are generated from the same stress. The model of FIG. 2B is applied to the changes over time of the strain $\varepsilon_c 1$ of the viscoelasticity measurement reference layer 3 and the strain $\varepsilon 11$ of the subject 4, so that the Young's modulus and the viscosity coefficient at the position of the strain $\varepsilon 11$ are calculated as described above. Further, the Young's modulus and the viscosity coefficient at the position of the strain $\varepsilon 12$ are calculated from the changes over time of the strain $\varepsilon_c 1$ of the viscoelasticity measurement reference layer 3 and the strain $\varepsilon 12$. In the same manner, the Young's modulus and the viscosity coefficient at positions aligned with the strain $\varepsilon_c 1$ of the viscoelasticity measurement reference layer 3 in the vertical direction are calculated. The same method is performed by using the values of the strains of the subject 4 aligned with each position of the strain distribution of the strains $\varepsilon_c 1$, $\varepsilon_c 2$, $\varepsilon_c 3$, and so forth of the viscoelasticity measurement reference layer 3 in the vertical direction, so that the Young's modulus and the viscosity coefficient of a cross-section can be calculated.

On the basis of the principle described above, the viscoelasticity measurement reference layer 3 whose viscosity coefficient and elastic modulus are known is provided between the conversion element array 2 that is a conversion device which receives an elastic wave reflected by the subject 4 and converts the elastic wave into an electrical signal and the subject 4, and the strain of the subject 4 and the strain of the reference layer 3 which are generated when a pressure is applied to the subject 4 and the reference layer 3 are measured on the basis of the elastic wave reflected by the subject 4. It is possible to calculate the viscosity coefficient of the subject by using the measured strain of the reference layer 3, the measured strain of the subject 4, and the known viscosity coefficient and elastic modulus of the reference layer 3.

As described above, the pressure applied to the subject 4 and the reference layer 3 is a periodic pressure including a release of the pressure, so that the viscoelasticity distribution calculation unit 8 that is a calculation unit can calculate the viscosity coefficient (1) of the subject 4 by using the change over time of the strain value of the subject 4 and the change over time of the strain value of the reference layer 3 which are generated by the periodic pressure.

Specifically, for example, as described in the above equation 6 to 8, the viscoelasticity distribution calculation unit 8 that is a calculation unit can calculate the viscosity coefficient ($\eta$) of the subject by using the area of the hysteresis loop drawn with the strain values of the subject 4 and the strain values of the reference layer 3 generated by the periodic pressure, or as described in the above equations 5, using the delay time between the change over time of the strain value of the subject 4 and the change over time of the strain value of the reference layer 3.

As described above, the pressure applied to the subject 4 and the reference layer 3 is instantaneously increased to a certain pressure and thereafter the certain pressure is held for a certain time period, so that the viscoelasticity distribution calculation unit 8 that is a calculation unit can calculate the viscosity coefficient ($\eta$) of the subject 4 by using the strain value of the subject 4 and the strain value of the reference layer 3 after the pressure applied to the subject 4 and the reference layer 3 is instantaneously increased to the certain pressure.

Although, in the above embodiment, the Young's modulus is used as elasticity characteristics and the viscosity coefficient is used as viscosity characteristics, an elastic coefficient such as a stiffness coefficient and a pressure elastic coefficient and a viscous coefficient such as a viscosity and a viscosity coefficient can be used. Further, here, a calculation method of the viscosity characteristics using a storage elastic modulus as the elasticity characteristics and a loss elastic modulus as the viscosity characteristics will be described. When a stress $\sigma(t)$ is applied to a material having viscoelastic characteristics, the phase of the strain $\varepsilon(t)$ is delayed from the phase of the strain.

$\sigma(t) = \sigma_0 \sin \omega t$ $\varepsilon(t) = \varepsilon_0 \sin(\omega t - \delta)$ δ represents a delay of the phase. At this time, a storage elastic modulus G', a loss elastic modulus G", and an absolute dynamic elastic modulus |G| can be represented by the equation below.

$$G' = |G|\cos\delta$$
$$G'' = |G|\sin\delta$$
$$|G| = \frac{\sigma_0}{\varepsilon_0} = \sqrt{G'^2 + G''^2}$$

Here, when the amplitude of strain of the viscoelasticity measurement reference layer is $\varepsilon_{c0}$, the amplitude of strain of the subject is $\varepsilon_{t0}$, and the phase difference between the strain of the viscoelasticity measurement reference layer and the strain of the subject is $\delta_{t-c}$, these three values can be measured by an ultrasonic wave. A storage elastic modulus of the viscoelasticity measurement reference layer $G_c'$, a loss elastic modulus of the viscoelasticity measurement reference layer $G_c''$, an absolute dynamic elastic modulus $|G_c|$, and a phase of strain of the viscoelasticity measurement reference layer $\delta_c$ are separately measured, so that these values become known parameters. When the values that can be measured by an ultrasonic wave and the known parameters are used, a phase of strain of the subject $\delta_t$, a storage elastic modulus of the subject $G_t'$, a loss elastic modulus of the subject $G_t''$ can be calculated by the equation below.

$$\delta_t = \delta_{t-c} + \delta_c$$
$$G_t' = |G_c|\frac{\varepsilon_{c0}}{\varepsilon_{t0}}\cos(\delta_{t-c} + \delta_c)$$
$$G_t'' = |G_c|\frac{\varepsilon_{c0}}{\varepsilon_{t0}}\sin(\delta_{t-c} + \delta_c)$$

In other words, the viscosity characteristics (loss elastic modulus) of the subject can be calculated by using the elasticity characteristics (storage elastic modulus) of the viscoelasticity measurement reference layer, the viscosity characteristics (loss elastic modulus) of the viscoelasticity measurement reference layer, and the strains of the viscoelasticity measurement reference layer and the subject. The storage elastic modulus and the loss elastic modulus calculated as described above are values that can be measured by a normal viscoelastic characteristic measuring device. For example, these values can be directly compared with mechanical measurement results of viscoelasticity measured using an extracted tissue.

Next, an example of the present invention will be described along with the constituent elements of the above embodiment on the basis of an example 1.

Example 1

Hereinafter, the example 1 of the present invention will be described with reference to the drawings. FIG. 1 is a block diagram showing the example of an ultrasonic diagnostic apparatus according to the present invention. The constituent elements will be sequentially described along with operations thereof.

[Specific Configuration Example of Viscoelasticity Measurement Reference Layer]

The viscoelasticity measurement reference layer 3 is formed of a material which propagates but does not absorb or scatter an ultrasonic wave as an elastic wave and which has shape retention property, flexibility, and appropriate elasticity. The propagation property of ultrasonic wave is important because image is formed by transmitting and receiving an ultrasonic wave through the viscoelasticity measurement reference layer 3. If the ultrasonic wave propagation is attenuated by absorption or scattering, efficiency of the transmission and reception degrades. Therefore, the viscoelasticity measurement reference layer 3 is formed of a uniform material which is transparent with respect to ultrasonic wave and which has a small attenuation constant and a propagation speed (sound speed) near the average sound speed in the subject 4. If the acoustic impedance of the viscoelasticity measurement reference layer 3 is largely different from that of the subject 4, reflection occurs on the boundary surface and efficiency of the transmission and reception for creating an image degrades, so that the acoustic impedance of the viscoelasticity measurement reference layer 3 is not so much different from that of the subject 4. However, if the acoustic impedance of the viscoelasticity measurement reference layer 3 is the same as that of the subject 4, it is difficult to detect the boundary surface described later, so that the acoustic impedance of the viscoelasticity measurement reference layer 3 is different from that of the subject 4 by an appropriate amount of acoustic impedance. The viscoelasticity measurement reference layer 3 has shape retention property, flexibility, and appropriate elasticity to measure the distribution of the stress (pressure) by using the amount of deformation of the viscoelasticity measurement reference layer 3. As a material having the above characteristics, aqueous gel such as polyvinyl alcohol, polyurethane, and rubber material can be used. However, any material having the above characteristics can be used. However, a material is used whose elastic coefficient such as Young's modulus, stiffness coefficient, and pressure elastic coefficient and viscous coefficient such as viscosity and viscosity coefficient are known. The thickness of the viscoelasticity measurement reference layer 3 should be thin in the viewpoint of the propagation of the ultrasonic wave. However, the viscoelasticity measurement reference layer 3 should be appropriately deformed to measure the distribution of the stress (pressure). Further, it is necessary for the viscoelasticity measurement reference layer 3 to be put in an area where the strain distribution is detected. Therefore, the thickness of the viscoelasticity measurement reference layer 3 is 0.1 mm to 50 mm, and preferably 1 mm to 10 mm.

[Creating Reception Beam Signal and Displaying B-Mode Image]

The probe 1 mechanically or electronically performs beam scan and transmits and receives an ultrasonic wave to and from the subject 4. The conversion element array 2 is a conversion device in which conversion elements which are driven by a drive waveform from the transmitting unit 5 and generate an ultrasonic wave are arranged. The transmitting unit 5 generates a drive waveform to each conversion element of the conversion element array 2 and adjusts the drive timing of each conversion element on the basis of control from the control unit 11. A synthesized ultrasonic wave obtained by synthesizing ultrasonic waves generated from each conversion element by adjusting the drive timing of the conversion elements forms an ultrasonic wave transmission beam that converges to a predetermined point. In other words, the control unit 11 controls the transmitting unit 5, so that the ultrasonic wave transmission beam having a convergence point at a desired depth and a directivity in a desired direction is transmitted from the probe 1. The control unit 11 performs sector scan in which the direction of the ultrasonic wave transmission beam is swung and beam scan is performed. Or, the conversion elements that are driven on the conversion element array 2 are limited to form a transmission opening and the transmission opening is moved, so that linear scan is performed in which the ultrasonic wave transmission beams scan in substantially parallel.

The receiving unit 6 includes a receiving circuit and a phasing addition circuit. The receiving circuit amplifies received signals that are received by each conversion element of the conversion element array 2 and converts the received signals into a plurality of time series digital signals by performing AD conversion. The phasing addition circuit is to form an ultrasonic wave reception beam. The phasing addition circuit provides and adds (phasing of) a delay time controlled by the control unit 11 to the digitalized received signals to form a reception beam signal. The reception beam signal is a signal in which received timing of the signals received by the conversion elements are adjusted and the signals are summed up and it is possible to form an ultrasonic wave reception beam having directivity with respect to the receiver sensitivity and one or a plurality of convergence points. The control unit 11 performs beam scan of the ultrasonic wave reception beam in synchronization with the ultrasonic wave transmission beam. As a result, a reception beam signal is obtained by transmitting an ultrasonic wave transmission beam into the subject 4 from the probe 1 and receiving an ultrasonic reflection echo signal reflected from an internal tissue of the subject 4 in an ultrasonic wave reception beam. By the beam scan of the control unit 11, a plurality of reception beam signals corresponding to ultrasonic reflection echo signals with respect to a specific point or a specific direction in the subject 4 are obtained. The reception beam signals are arranged corresponding to the beam scan, so that a cross-sectional image corresponding to the intensity of the ultrasonic reflection echo signals in the subject 4 is obtained. The control unit 11 repeats the beam scan, so that cross-sectional images at different times of day are obtained.

A plurality of reception beam signals generated by the receiving unit 6 are inputted into the imaging unit 9. The imaging unit 9 forms a gray scale B-mode cross-sectional image reflecting the cross-sectional structure in the subject 4 from the plurality of reception beam signals. The imaging unit 9 arranges the plurality of reception beam signals according to the beam scan and performs signal processing, such as gain correction, filter processing, envelope demodulation, and log compression, on the reception beam signals. Further, the imaging unit 9 may include a digital scan conversion circuit for converting the signals into a display signal to the display unit 10 by performing image processing such as unsharp mask and image filter for displaying image after the signal processing and a DA conversion circuit for analog video signal. The imaging unit 9 causes the display unit 10 to display a B-mode cross-sectional image according to display control from the control unit 11.

The display unit 10 is a display apparatus such as CRT and LCD. The display unit 10 displays an image based on the display signal from the imaging unit 9.

[Specific Configuration Example of a Strain Detecting Unit which is a Measuring Unit for Measuring Strain]

The plurality of reception beam signals generated by the receiving unit 6 are also inputted into the strain distribution detecting unit 7. The strain distribution detecting unit 7 that is a measuring unit for measuring strain detects strain distributions in the subject 4 and the viscoelasticity measurement reference layer 3 on the basis of the plurality of reception beam signals.

The strain distribution can be detected by performing correlation calculation between reception beam signals at the same position obtained in different beam scan periods in the same manner as in the known color-flow Doppler method and tissue tracking method.

The strain distribution detecting unit 7 has a memory circuit for storing the plurality of reception beam signals and a correlation calculation circuit. The plurality of reception beam signals obtained when the control unit 11 repeats the beam scan are stored in the memory circuit. A set of reception beam signals obtained by one beam scan forms frame reception beam signal data corresponding to a cross-sectional image at a certain time point. Different frame reception beam signal data corresponds to a beam scan at a different time point. (Each frame reception signal data includes reception beam signals from a plurality of different positions.) Reception beam signals at a corresponding position between different frame reception beam signal data are ultrasonic reflection echo signals from the same position between beam scans at different time points. Therefore, a displacement at the corresponding position generated between beam scans at different time points can be measured by performing correlation calculation of these reception beam signals. The strain distribution is calculated from the displacement distribution in taking the difference along beam depth direction.

The correlation calculation circuit has a Hilbert transform filter at the input portion thereof. The correlation calculation circuit converts two reception beam signals of beam scans at different time points corresponding to the same position into an analysis signal and performs complex correlation calculation of these signals. Or, by using an I-Q signal obtained by quadrature detection of the reception beam signal, an instantaneous phase delay in time series between two reception beam signals of beam scans at different time points corresponding to the same position is calculated, and displacement may be obtained by converting the instantaneous phase delay into a sound speed. Further, the accuracy of the strain measurement may be improved by using a combined autocorrelation method or the like known in the related technical field.

As a specific configuration of the memory circuit and the correlation calculation circuit, the configuration described below may be used.

A first example includes a memory unit that stores a plurality of frame reception beam signal data and a plurality of correlation calculation circuits corresponding to beam positions used in one beam scan. Two frame reception beam signal data corresponding to beam scans at different time points are selected from a plurality of frame reception beam signal data stored in the memory circuit and reception beam signals corresponding to the two frame reception beam signal data are inputted into correlation calculation circuits corresponding to each beam position. A displacement amount distribution in the beam depth direction at a corresponding beam position can be obtained by performing correlation calculation in the correlation calculation circuit. In this configuration, beam scan is repeatedly performed and correlation calculation is performed by selecting frame reception beam signal data from a plurality of obtained frame reception beam signal data, so that it is possible to measure a displacement between beam scans at any two time points. The amount of strain can be measured by calculating a difference between the strains in the depth direction.

Here, a plurality of correlation circuits that perform one-dimensional correlation calculation for each beam position are used. However, it is possible to use a correlation circuit that performs two-dimensional correlation calculation for frame reception beam signal data at different time points of beam scan.

Another example includes a plurality of memory circuits and a plurality of correlation calculation circuits corresponding to each beam position used in beam scan. Each of the plurality of memory circuits includes two FIFO type memories and a TMP memory for primarily storing a correlation calculation result. While the beam scan is repeatedly performed, reception beam signals are first stored in first FIFO type memories for each beam position. An output of the first FIFO type memory is inputted into a second FIFO type memory and the correlation calculation circuit. Further, an output of the second FIFO type memory is inputted into the correlation calculation circuit. Each of the two FIFO type memories has a memory capacity for storing a reception beam signal obtained at a beam position corresponding to each beam scan. Therefore, at a certain time point in repetitive beam scans, two reception beam signals at beam positions corresponding to two temporally consecutive beam scans are stored. The two reception beam signals are calculated by the correlation calculation circuit and the displacement amount distribution in the beam depth direction at a corresponding beam position is obtained. The displacement amount distribution obtained here is generated between the two temporally consecutive beam scans in the repetitive beam scans. To obtain displacement generated between a plurality of beam scans, the calculation result of the correlation calculation circuit is accumulatively added. Therefore, the calculation result of the correlation calculation is added to data in the TMP memory and the addition result is stored in the TMP memory. Further, the strain distribution is calculated by calculating differences of the displacement distribution in the depth direction. This configuration is suited to implement the strain distribution detecting unit 7 by pipeline type processing suitable to real time processing. In particular, in this configuration, the capacity of the memory circuit can be smaller than that of the example described above.

In both examples described above, the strain distribution in the beam depth direction generated between different beam scans is obtained from a plurality of correlation calculation circuits corresponding to each beam position. The strain distributions are arranged in each beam position, so that a strain distribution of two-dimensional cross-sectional image generated between different beam scans is obtained. In addition to the two examples described above, it is possible to detect a strain distribution of two-dimensional cross-section using frame reception beam signal data obtained by beam scans at different time points by using a method known in the related art.

In the present example, in particular, an area including not only the subject 4, but also the viscoelasticity measurement reference layer 3 is used to measure the strain distribution. More specifically, the area is set so that the amount of displacement in a boundary portion between the subject 4 and the viscoelasticity measurement reference layer 3 is measured. Thereby, the strain distribution of the viscoelasticity measurement reference layer 3 is calculated. To detect the amount of displacement in the viscoelasticity measurement reference layer 3, a reception beam signal is cut out so that the reception beam signal includes a reflection echo of ultrasonic wave from the boundary portion and a series of correlation calculations described above may be performed. However, the calculation circuit as described below can be separately provided.

Generally, inside of the viscoelasticity measurement reference layer 3 is substantially transparent with respect to ultrasonic waves, so that a reflection echo signal of ultrasonic wave is very small and the reception beam signal is also very small. Therefore, the correlation calculation result of the reception beam signal in this area includes an error and the result may be unstable. On the other hand, the boundary portion between the subject 4 and the viscoelasticity measurement reference layer 3 locally generates a large reflection echo signal due to a difference of acoustic impedance between the subject 4 and the viscoelasticity measurement reference layer 3, so that the reception beam signal and the correlation calculation result thereof can be accurately detected. The viscoelasticity measurement reference layer 3 is formed of a material uniform in the thickness direction and has a strain distribution constant in the thickness direction, so that a strain distribution in the layer is obtained by using the strain values obtained from the displacement in the boundary portion.

Therefore, a threshold circuit is provided at an input portion of the correlation calculation circuit and a reception beam signal whose intensity is smaller than a certain value is set to 0, so that the correlation calculation is performed by masking a front portion and a portion corresponding to the thickness of the viscoelasticity measurement reference layer 3 of each reception beam signal. Thus, instability as described above can be eliminated.

Further, a portion in which the amplitude intensity of the reception beam signal is smaller than a certain value is determined to be inside of the viscoelasticity measurement reference layer 3, so that the boundary portion of the reception beam signal is directly detected and displacement in the boundary portion between beam scans whose boundary portion position is different may be obtained from a difference between the frame reception beam signal data of the beam scans. The strain distribution of the viscoelasticity measurement reference layer 3 may be calculated from displacement distribution of the boundary portion between the subject 4 and the viscoelasticity measurement reference layer 3, in taking the difference along the depth direction.

As described above, the amount of strain of the viscoelasticity measurement reference layer 3 is calculated from a front portion of each reception beam signal and the strain distribution of the subject 4 along the depth direction is calculated from a portion following the front portion. The strain distributions along the depth direction calculated from the reception beam signals are arranged at corresponding beam positions, so that a cross-section strain distribution of the subject 4 and a strain distribution of the viscoelasticity measurement reference layer 3 along the boundary between the viscoelasticity measurement reference layer 3 and the subject 4 are measured. These strain distributions are inputted from the strain distribution detecting unit 7 to the viscoelasticity distribution calculation unit 8, which is a unit for calculating the viscosity coefficient.

[Viscoelasticity Distribution Calculation Unit which is a Unit for Calculating the Viscosity Coefficient]

The viscoelasticity distribution calculation unit 8, which is a unit for calculating the viscosity coefficient, calculates the elastic modulus distribution and the viscosity coefficient distribution in the subject 4 from the strain distributions of the viscoelasticity measurement reference layer 3 and the subject 4 and the elastic coefficient and the viscous coefficient of the viscoelasticity measurement reference layer 3 according to the principle described above.

The viscoelasticity distribution calculation unit 8 may be formed by using a microprocessor, a memory, a control circuit that controls the microprocessor and the memory, and a bus circuit that transmits data, or may be implemented as processing software on a programmable processing circuit such as a general-purpose PC and an FPGA.

Therefore, the process in the viscoelasticity distribution calculation unit 8 will be described below. When linear scan of an ultrasonic beam is performed to measure strain, each position of the ultrasonic beams corresponding to each reception beam signal substantially corresponds to a direction in which pressure is applied. Therefore, the amount of strain of the viscoelasticity measurement reference layer 3 obtained for each reception beam signal and the strain distribution of the subject 4 along the depth direction correspond to strains in the same column aligned in the vertical direction described in FIG. 4. Therefore, the process including the process of the strain distribution detecting unit 7 can be performed for each reception beam signal. When sector scan of the ultrasonic beam is performed or when another scan is performed, by using a geometric relationship between the position of the ultrasonic beam when scan is performed and the direction in which pressure is applied, an arrangement of the amount of strain of the viscoelasticity measurement reference layer 3 and the strain distribution of the subject 4 along the depth direction is generated for each column aligned in the vertical direction described in FIG. 4. At this time, an arrangement of the strain distribution of the subject 4 is generated from a positional relationship between the position of the ultrasonic beam and the column aligned in the vertical direction by interpolation calculation. For simplicity of the description, an example in which linear scan is performed will be described below. However, the same process can be performed for other beam scan methods by replacing the arrangement of the amount of strain of the viscoelasticity measurement reference layer 3 and the strain distribution of the subject 4 along the depth direction which is generated for each reception beam signal by a data string aligned in the vertical direction from the above positional relationship.

For each frame reception beam signal data obtained by one beam scan, a cross-sectional strain distribution data set at the frame time of the beam scan is obtained. The cross-sectional strain distribution data set includes the amount of strain of the viscoelasticity measurement reference layer 3 and a string of strain values along the depth direction of the subject 4 obtained from each reception beam signal at the time corresponding to one beam scan. The data set of the amount of strain of the viscoelasticity measurement reference layer 3 and the strain values along the depth direction of the subject 4 for each reception beam signal is referred to as a beam strain distribution data set. The cross-sectional strain distribution data set includes a plurality of beam strain distribution data sets corresponding to each reception beam signal at each time. In the cross-sectional strain distribution data set, each beam strain distribution data set corresponds to an ultrasonic beam position in a beam scan. A plurality of cross-sectional strain distribution data sets corresponding to scans at different times can be obtained by repeating beam scan.

Cross-sectional strain distribution data sets at each time can be obtained by repeating beam scan while periodically applying pressure.

The area S1 of viscoelasticity measurement reference layer strain–subject strain hysteresis loop is calculated from a plurality of cross-sectional strain distribution data sets obtained when one cycle or a plurality of cycles of application of pressure is completed. The maximum strain $\varepsilon_{cmax}$ and the minimum strain $\varepsilon_{cmin}$ of the viscoelasticity measurement reference layer 3 are calculated for each ultrasonic beam position from a corresponding beam strain distribution data set. (A beam strain distribution data set corresponding to a desired ultrasonic beam position is extracted from the cross-sectional strain distribution data sets of each time point obtained during one cycle of application of pressure, and a maximum value and a minimum value of the strain of the viscoelasticity measurement reference layer 3 in the data set are obtained. The above operation is performed for each ultrasonic beam position. An average value of the strain values of the viscoelasticity measurement reference layer 3 in one cycle of application of pressure may be calculated by using the cross-sectional strain distribution data sets obtained during a plurality of cycles of application of pressure, and the maximum value and the minimum value in one cycle may be obtained. As the maximum value and the minimum value, values in the beam strain distribution data set, that is, values obtained at a time point when the data is obtained at each scan, may be used. Or, values may be interpolated between these values with respect to time, and an interpolated value of a time point between time points when data is actually obtained may be estimated as the maximum value or the minimum value.) For each ultrasonic beam position, viscoelasticity measurement reference layer strain amplitude $\varepsilon_c$ is calculated from a difference between the maximum strain $\varepsilon_{cmax}$ and the minimum strain $\varepsilon_{cmin}$. Next, the area S1 of the viscoelasticity measurement reference layer strain–subject strain hysteresis loop is calculated for each point in the depth direction in each ultrasonic beam position. First, an outward area is obtained by, from a strain value of the subject and a strain value of the viscoelasticity measurement reference layer at the time point along from a time when the minimum strain $\varepsilon_{cmin}$ is given to a time when the maximum strain $\varepsilon_{cmax}$ is given. (The strain value of the subject is given for a point at each depth in the beam strain distribution data and the strain value of the viscoelasticity measurement reference layer is given for each beam strain distribution data to which the point belongs. Therefore, a pair of the strain value of the subject and the strain value of the viscoelasticity measurement reference layer at each time for a point at each depth of the beam position is obtained. For example, trapezoidal integration approximation or Simpson integral approximation and the area S1 are obtained from the pair of these values of each time point.) Next, similarly, a return area is obtained along from the time when the maximum strain $\varepsilon_{cmax}$ is given to the time when the minimum strain $\varepsilon_{cmin}$ is given and a difference between the outward area and the return area is calculated, so that the area S1 of the viscoelasticity measurement reference layer strain–subject strain hysteresis loop is obtained. At the same time, a maximum strain $\varepsilon_{max}$ and a minimum strain $\varepsilon_{min}$ of the subject are calculated at each point and viscoelasticity measurement reference layer strain amplitude E is calculated from the difference between them. Then, the elastic modulus and the viscosity coefficient at each point are calculated by reversely solving (Equation 8).

Accuracy of data for calculating the hysteresis loop area can be improved by repeating a plurality of cycles of pressure application. Specifically, the area is calculated by using all pairs of the viscoelasticity measurement reference layer strain and the subject strain which are obtained at each point and each time. In this case, the pairs obtained in a process in which the viscoelasticity measurement reference layer strain increases as time advances are used for calculating the outward area and the pairs obtained in a process in which the viscoelasticity measurement reference layer strain decreases as time advances are used for calculating the return area. Regarding the maximum strain and the minimum strain, similarly, the maximum value and the minimum value of the strains measured across the entire measurement time may be used. The area S1 of the viscoelasticity measurement reference layer strain–subject strain hysteresis loop may be calculated for each pressure cycle and an average value of the area S1 may be used.

Further, a part of the amounts of strain of the viscoelasticity measurement reference layer 3 or an average strain value in the beam strain distribution data set is calculated and a pressure cycle time T may be calculated by measuring change over time of the average strain value. In other words, the pressure cycle time T can be obtained by calculating a time difference between time points of the maximum value and the minimum value of the average strain value changing over time in a process in which periodic pressure is applied. When a plurality of cycles of pressure is applied, the pressure cycle time T may be obtained by calculating an average value of the pressure cycle times. Although a part or an average of the amounts of strain of the viscoelasticity measurement reference layer 3 is used as the average strain value, an amount of strain in a specific position in the subject 4 or an average of the amounts of strain in the subject 4 may be used.

Distributions of the elastic modulus and the viscosity coefficient in a cross-section of the subject are calculated by performing the above calculation for all points in the depth direction in the ultrasonic beam position and for all the ultrasonic beam positions in the beam scan.

The calculated distribution data of elastic modulus and viscosity coefficient is inputted into the imaging unit 9. The imaging unit 9 forms a viscoelasticity cross-sectional image reflecting the viscoelasticity in the subject 4 from a plurality of distribution data of elastic modulus and viscosity coefficient. In the same manner as forming the B-mode cross-sectional image, the imaging unit 9 performs signal processing such as gain correction and filter processing and image processing such as unsharp mask and image filter to form the viscoelasticity cross-sectional image. Further, the imaging unit 9 causes the display unit 10 to display the viscoelasticity cross-sectional image along with the B-mode cross-sectional image by style such as switching, simultaneous parallel, and superimposed synthetic according to display control from the control unit 11. Further, the imaging unit 9 may generate a strain cross-sectional image on the basis of the strain distribution data in the subject 4 generated by the strain distribution detecting unit 7 and cause the display unit 10 to display the viscoelasticity cross-sectional image along with the B-mode cross-sectional image by style such as switching, simultaneous parallel, and superimposed synthetic according to display control from the control unit 11. The elastic modulus and the viscosity coefficient may be assigned to any one of hue, chroma, and brightness respectively and displayed. By such a display, it is possible to intuitively observe the two physical properties such as the elastic modulus and the viscosity coefficient. Further, when the elastic modulus and the viscosity coefficient are superimposed on the B-mode cross-sectional image, a degree of transparency which reflects one or both of the elastic modulus and the viscosity coefficient may be set and superimposed. By such a superimposition, it is possible to efficiently observe an area having a noticeable elastic modulus or viscosity coefficient.

[Viscoelasticity Distribution Measurement Operation and Display of Viscoelasticity Cross-Sectional Image]

Next, the process performed by the control unit 11 when the viscoelasticity distribution measurement is performed will be described. As described above, the control unit 11 performs control of ultrasonic wave transmission/reception scan and causes the display unit 10 to display the B-mode cross-sectional image. At this time, the control unit 11 may cause the strain distribution detecting unit 7 to operate and display the strain cross-sectional image on the display unit 10 along with the B-mode cross-sectional image or instead of the B-mode cross-sectional depending on an input.

When a user disposes the probe 1 on a predetermined portion of the subject 4 while checking the B-mode cross-sectional image on the display unit 10 and turns on the control switch 12, the control unit 11 starts the process of the viscoelasticity distribution calculation unit 8 and the viscoelasticity distribution measurement operation starts. While the user applies periodical pressure to the subject 4 via the probe 1, the viscoelasticity distribution calculation unit 8 operates and generates a cross-sectional strain distribution data set for each time point. When a plurality of cycles of pressure is applied, the user inputs a cycle period signal from the control switch 12 at the start of a cycle and the end of a cycle. The control unit 11 calculates the pressure cycle T from the inputs of the cycle period signals and inputs the pressure cycle T into the viscoelasticity distribution calculation unit 8. When the periodical pressure application is completed, by turning off the control switch 12, generation of the cross-sectional strain distribution data set in the viscoelasticity distribution calculation unit 8 ends, the area S1 of the viscoelasticity measurement reference layer strain–subject strain hysteresis loop is calculated, and the Distributions of the elastic modulus and the viscosity coefficient are calculated. When the calculation process is completed, the control unit 11 causes the imaging unit 9 to operate and generate a viscoelasticity cross-sectional image and causes the display unit 10 to display the viscoelasticity cross-sectional image according to a display style inputted in advance.

Although, here, start and end of the pressure cycle are inputted from the control switch 12, it is not necessary to input the cycle period signal if the pressure cycle T is obtained from a change over time of one of strains in the obtained cross-sectional strain distribution data set in the viscoelasticity distribution calculation unit 8 as described above.

Further, although the area S1 of the viscoelasticity measurement reference layer strain–subject strain hysteresis loop is calculated after all the cross-sectional strain distribution data sets are obtained, it is possible to specify the number of data acquisition pressure cycles and start calculation of the area S1 of the viscoelasticity measurement reference layer strain–subject strain hysteresis loop, the elastic modulus, and the viscosity coefficient after the specified number of pressure cycles are completed. The area of the hysteresis loop, the elastic modulus, and the viscosity coefficient are calculated while the cross-sectional strain distribution data set to be used is updated, so that the distributions of the elastic modulus and the viscosity coefficient can be calculated over time, and at the same time, the viscoelasticity cross-sectional image can be updated for each pressure cycle.

Although, in the above description, the elastic modulus and the viscosity coefficient are calculated by using the area S1 of the viscoelasticity measurement reference layer strain–subject strain hysteresis loop, the elastic modulus and the viscosity coefficient may be calculated by using the hysteresis parameter.

It is possible to calculate the viscoelasticity measurement reference layer strain amplitude $\varepsilon_c$ and calculate the stress amplitude $\sigma_0$ at a beam position corresponding to each beam strain distribution data by using (Equation 3). Thereafter, a delay time between the change of the viscoelasticity measurement reference layer strain and the strain change in the subject at each point may be calculated from changes over time of the viscoelasticity measurement reference layer strain at the beam position and the strains in the subject arranged in the depth direction in the beam position, and the elastic modulus and the viscosity coefficient may be calculated by using (Equation 5). (The delay time may be obtained from a difference of times when the strain value of subject and the strain value of viscoelasticity measurement reference layer reach the maximum value and/or the minimum value respectively. Here, the strain value of subject is obtained for each point in the subject, and a strain value of viscoelasticity measurement reference layer obtained with respect to a beam position to which the point belongs is used.) Or, the delay time may be obtained by performing a cross-correlation calculation on time-series data of the strain of the viscoelasticity measurement reference layer and the strain of the subject which change for each point.

Although, in the present example, a user applies periodic pressure by using a hand-held type probe, it is possible to automatically apply periodic pressure by attaching an excitation unit such as a micro motor to the hand-held type probe or providing a separate pressing unit for pressing the probe and driving the excitation unit or the separate pressing unit from the control unit 11. In this configuration, it is possible to accurately control a change over time of pressure application, such as the pressure cycle $\tau$ which is periodically applied, so that the calculation accuracy of the elastic modulus and the viscosity coefficient can be improved.

Furthermore, although, in the above description, the viscoelasticity measurement reference layer 3 is included in the probe 1, the viscoelasticity measurement reference layer 3 can be formed as an attachable and detachable coupler separate from the probe 1. The shape and the viscoelasticity of the coupler can be selected according to a region to be diagnosed. In this case, in the control unit 11, the elastic modulus and the viscosity coefficient can be inputted or selected according to the type of the coupler, and the viscoelasticity distribution calculation unit 8 may calculate the distribution of the elastic modulus and the viscosity coefficient of the subject by using the selected values.

Example 2

In the present example, pressure is not periodically applied but applied in a step-like manner. The difference from the example 1 is mainly the process of the viscoelasticity distribution calculation unit 8, so that the process of the viscoelasticity distribution calculation unit 8 will be mainly described and only the difference will described.

When the control switch 12 of the probe 1 is turned on, the control unit 11 controls the viscoelasticity distribution calculation unit 8 so that the cross-sectional strain distribution data set is stored corresponding to each time point of the beam scan. The probe 1 is instantaneously pressed in a step-like manner to a certain pressure level by a manual operation or a pressing unit and the pressure is held until data acquisition is completed. The viscoelasticity distribution calculation unit 8 uses (Equation 10) and a change over time of strain of the viscoelasticity measurement reference layer 3 of each beam strain distribution data set obtained at different time points thereafter and calculates the stress amplitude $\sigma_0$ at a corresponding beam position (When Equation 10 is used, the stress amplitude $\sigma_0$ may be obtained by applying the strain value of the viscoelasticity measurement reference layer 3 obtained after a specific time interval from the step-like pressure application, a known Young's modulus of the viscoelasticity measurement reference layer 3, and a value of $\tau_c$ obtained from the Young's modulus and a known viscosity coefficient to (Equation 10)). However, it is desired to improve measurement accuracy by using time intervals of a plurality of points and fitting to (Equation 10).

By using subject strain values in each beam strain distribution data set in a plurality of cross-sectional strain distribution data sets obtained at different time points, a change over time of subject strain at each position in the depth direction at corresponding beam positions is extracted. The ratio $\tau$ of the Young's modulus and the viscosity coefficient at each point in the subject is calculated from the change over time at each point by using (Equation 12). First, to calculate a differential of the subject strain, an approximate time differential value of the strain is calculated by dividing an increment of the subject strain for each specific time interval from the step-like pressure application corresponding to each cross-sectional strain distribution data set by the time interval, and $1/\tau$ is obtained from the inclination of the change over time of the approximate time differential value of the strain according to (Equation 12). Also at this time, it is desired to obtain $1/\tau$ from the approximate differential value of strain at a plurality of time points by fitting. At the same time, the value of the following expression is obtained from an intercept of a change over time of the approximate time differential value of the strain.

[Math. 13]

$$\ln\left(\frac{\sigma_0}{\tau E}\right)$$

Then, the Young's modulus E is obtained from T obtained in the above calculation and the stress amplitude $\sigma_0$.

Distributions of the elastic modulus and the viscosity coefficient in a cross-section of the subject are calculated by performing the above calculation for all points in the depth direction in the ultrasonic beam position and for all the ultrasonic beam positions in the beam scan.

The calculated distributions of the elastic modulus and the viscosity coefficient are inputted into the imaging unit 9 in the same manner as in the example 1 and the viscoelasticity cross-sectional image is displayed on the display unit 10.

Although, here, the approximate time differential value is obtained by dividing an increment of the subject strain by the time interval, a high-order central difference, forward difference, or backward difference may be used.

In the present example, the Young's modulus and the viscosity coefficient of the subject are obtained from a change over time of strains in the subject and the viscoelasticity measurement reference layer against the step-like pressure application. In this case, regarding necessary time series time intervals, a sufficiently accurate calculation can be performed by using data at several to several tens of time points including a case in which the data is used for the fitting described above. Thereby, the necessary number of cross-sectional strain distribution data sets for each time point is several to several tens, and the frame reception beam signal data used to generate the cross-sectional strain distribution data sets includes several to several tens of frames. The beam scan for generating these data is completed within one to several seconds, so that there is an advantage that data used to generate viscoelasticity distribution data is acquired in a short time period. Also there is an advantage that measurement data can be acquired in a short time period without performing pressure application and pressure release, which are performed in the example 1.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A subject information acquisition apparatus for transmitting, through a reference layer, an elastic wave to a subject, receiving, through the reference layer, the elastic wave reflected from inside the subject, and acquiring information inside the subject, the subject information acquisition apparatus comprising:
a conversion device configured to receive the elastic wave and convert the elastic wave into an electrical signal; and
a memory and processor which function as each unit comprising:
a measuring unit configured to measure strain of the subject and strain of the reference layer which are generated when a pressure is applied to the subject and the reference layer interposed between the conversion device and the subject by using the electrical signal; and
a calculation unit configured to calculate a viscosity coefficient (TO) of the subject by using a viscosity coefficient and an elastic modulus of the reference layer, the strain of the subject, and the strain of the reference layer,
wherein
the pressure applied to the subject and the reference layer is periodic pressure application including releasing the pressure, and
the calculation unit calculates the viscosity coefficient ($\eta$) of the subject by using an area of a hysteresis loop drawn with strain values of the subject and strain values of the reference layer which are generated by the periodic pressure.

2. The subject information acquisition apparatus according to claim 1, wherein in a case the periodic pressure application is repeatedly performed, the calculation unit calculates an area of the hysteresis loop for each period, and averages the calculated areas.

3. The subject information acquisition apparatus according to claim 2, wherein
the pressure applied to the subject and the reference layer is instantaneously increased to a certain pressure and thereafter the certain pressure is held for a certain time period, and
the calculation unit calculates the viscosity coefficient ($\eta$) of the subject by using a strain value of the subject and a strain value of the reference layer after the pressure applied to the subject and the reference layer is instantaneously increased to a certain pressure.

4. The subject information acquisition apparatus according to claim 1, further comprising a control unit configured to display on a display unit a cross-sectional image of inside of the subject based on the electric signals and an image related to viscosity of the subject.

5. The subject information acquisition apparatus according to claim 4, wherein the control unit displays on the display unit, the cross-sectional image and the image related to viscosity of the subject in parallel, switching, or an overlaid manner.

6. A subject information acquisition apparatus for transmitting, through a reference layer, an elastic wave to a subject, receiving, through the reference layer, the elastic wave reflected from inside the subject, and acquiring information inside the subject, the subject information acquisition apparatus comprising:
a conversion device configured to receive the elastic wave and convert the elastic wave into an electrical signal; and
a memory and processor which function as each unit comprising:
a measuring unit configured to measure strain of the subject and strain of the reference layer which are generated when a pressure is applied to the subject and the reference layer interposed between the conversion device and the subject by using the electrical signal, the reference layer having a viscosity coefficient and an elastic modulus; and
a calculation unit configured to calculate a viscosity coefficient (TO) of the subject by using the viscosity coefficient and the elastic modulus of the reference layer, the strain of the subject, and the strain of the reference layer,
wherein
the calculation unit calculates the viscosity coefficient ($\eta$) of the subject by using a delay time between the change over time of the strain value of the subject and the change over time of the strain value of the reference layer which are generated by the application of the pressure.

7. The subject information acquisition apparatus according to claim 6, further comprising a control unit configured to display on a display unit a cross-sectional image of inside of the subject based on the electric signals and an image related to viscosity of the subject.

8. The subject information acquisition apparatus according to claim 7, wherein the control unit displays on the display unit, the cross-sectional image and the image related to viscosity of the subject in parallel, switching, or an overlaid manner.

9. A subject information acquisition apparatus for transmitting, through a reference layer, an elastic wave to a subject, receiving, through the reference layer, the elastic wave reflected from inside the subject, and acquiring information inside the subject, the subject information acquisition apparatus comprising:
a conversion device configured to receive the elastic wave and convert the elastic wave into an electrical signal; and
a memory and processor which function as each unit comprising:
a measuring unit configured to measure strain of the subject and strain of the reference layer which are generated when a pressure is applied to the subject and the reference layer interposed between the conversion device and the subject by using the electrical signal; and
a calculation unit configured to calculate a stress applied to the subject by using a viscosity coefficient of the reference layer, a Young's modulus of the reference layer, and the strain of the reference layer, according to the following equation:

$$\sigma(t) = E_c \varepsilon_c(t) + \eta_c \frac{d\varepsilon_c(t)}{dt},$$

where σ(t) and $\varepsilon_c(t)$ are changes over time t of the stress σ and the strain $\varepsilon_c$ of the reference layer, and $E_c$ and $\eta_c$ are respectively the Young's modulus and viscosity coefficient of the reference layer.

10. The subject information acquisition apparatus according to claim 9, wherein the calculation unit is further configured to calculate a viscosity coefficient (η) of the subject by using the calculated stress and using an area of a hysteresis loop drawn with strain values of the subject.

11. The subject information acquisition apparatus according to claim 9, further comprising an imaging unit that generates a viscoelasticity cross-sectional image of the subject.

12. The subject information acquisition apparatus according to claim 11, wherein the imaging unit causes a display unit to display the viscoelasticity cross-sectional image, the elastic modulus and the viscosity coefficient being respectively assigned to any one of hue, chroma, and brightness.

13. A subject information acquisition method for acquiring information on inside of a subject by using echo signals from the subject, the method comprising:
  transmitting, through a reference layer, an elastic wave to the subject;
  receiving, through the reference layer, the elastic wave reflected in the subject;
  measuring strain of the subject and strain of the reference layer which are generated when a pressure is applied to the subject and the reference layer; and
  calculating a viscosity coefficient (η) of the subject by using a viscosity coefficient and an elastic modulus of the reference layer, the strain of the subject, and the strain of the reference layer,
  wherein
  the pressure applied to the subject and the reference layer is periodic pressure application including releasing the pressure, and
  calculating the viscosity coefficient (η) of the subject is performed by using an area of a hysteresis loop drawn with strain values of the subject and strain values of the reference layer which are generated by the periodic pressure.

14. The method according to claim 13, wherein in a case the periodic pressure application is repeatedly performed,
  calculating the viscosity coefficient includes calculating an area of the hysteresis loop for each period and averaging the calculated areas.

15. The method according to claim 14, wherein in a case the pressure applied to the subject and the reference layer is instantaneously increased to a certain pressure and thereafter the certain pressure is held for a certain time period,
  the viscosity coefficient (η) of the subject is calculated by using a strain value of the subject and a strain value of the reference layer after the pressure applied to the subject and the reference layer is instantaneously increased to a certain pressure.

16. The method according to claim 13, further comprising:
  displaying on a display unit a cross-sectional image of inside of the subject based on obtained by the receiving and an image related to viscosity of the subject.

17. The method according to claim 16, wherein the displaying includes displaying the cross-sectional image and the image related to viscosity of the subject in parallel, switching, or an overlaid manner.

18. A subject information acquisition method for acquiring information on inside of a subject by using echo signals from the subject, the method comprising:
  transmitting, through a reference layer, an elastic wave to the subject;
  receiving, through the reference layer, the elastic wave reflected in the subject;
  measuring strain of the subject and strain of the reference layer which are generated when a pressure is applied to the subject and the reference layer; and
  calculating a viscosity coefficient (η) of the subject by using a viscosity coefficient and an elastic modulus of the reference layer, the strain of the subject, and the strain of the reference layer,
  wherein
  calculating the viscosity coefficient (η) of the subject is performed by using a delay time between the change over time of the strain value of the subject and the change over time of the strain value of the reference layer which are generated by the application of the pressure.

19. The method according to claim 18, further comprising:
  displaying on a display unit a cross-sectional image of inside of the subject based on signals obtained by the receiving and an image related to viscosity of the subject.

20. The method according to claim 19, wherein the displaying includes displaying the cross-sectional image and the image related to viscosity of the subject in parallel, switching, or an overlaid manner.

21. A subject information acquisition method for acquiring information on inside of a subject by using echo signals from the subject, the method comprising:
  transmitting, through a reference layer, an elastic wave to the subject;
  receiving, through the reference layer, the elastic wave reflected in the subject;
  measuring strain of the subject and strain of the reference layer which are generated when a pressure is applied to the subject and the reference layer; and
  calculating a stress applied to the subject by using a viscosity coefficient of the reference layer, a Young's modulus of the reference layer, and the strain of the reference layer, according to the following equation:

$$\sigma(t) = E_c \varepsilon_c(t) + \eta_c \frac{d\varepsilon_c(t)}{dt},$$

where σ(t) and $\varepsilon_c(t)$ are changes over time t of the stress σ and the strain $\varepsilon_c$ of the reference layer, and $E_c$ and $\eta_c$ are respectively the Young's modulus and viscosity coefficient of the reference layer.

22. The method according to claim 21, further comprising calculating a viscosity coefficient (TO) of the subject by using the calculated stress and using an area of a hysteresis loop drawn with strain values of the subject.

23. The method according to claim 21, further comprising generating a viscoelasticity cross-sectional image of the subject.

24. The method according to claim 23, further comprising displaying the viscoelasticity cross-sectional image, the elastic modulus and the viscosity coefficient being respectively assigned to any one of hue, chroma, and brightness.

* * * * *